(12) United States Patent
Minagawa

(10) Patent No.: US 9,738,744 B2
(45) Date of Patent: Aug. 22, 2017

(54) SURFACE MODIFICATION METHOD FOR THREE-DIMENSIONAL OBJECT AND SYRINGE GASKET

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days.

(21) Appl. No.: 14/891,034

(22) PCT Filed: Dec. 3, 2013

(86) PCT No.: PCT/JP2013/082409
§ 371 (c)(1),
(2) Date: Nov. 13, 2015

(87) PCT Pub. No.: WO2014/199529
PCT Pub. Date: Dec. 18, 2014

(65) Prior Publication Data
US 2016/0083497 A1    Mar. 24, 2016

(30) Foreign Application Priority Data

Jun. 11, 2013  (JP) ................................. 2013-123014
Aug. 9, 2013   (JP) ................................. 2013-166628

(51) Int. Cl.
| | |
|---|---|
| C08F 2/46 | (2006.01) |
| C08G 61/04 | (2006.01) |
| C08F 279/02 | (2006.01) |
| C08F 2/48 | (2006.01) |
| A61M 5/315 | (2006.01) |
| C08J 7/18 | (2006.01) |
| B05D 3/06 | (2006.01) |
| B05D 5/00 | (2006.01) |
| B05D 7/00 | (2006.01) |

(52) U.S. Cl.
CPC ....... *C08F 279/02* (2013.01); *A61M 5/31513* (2013.01); *B05D 3/067* (2013.01); *B05D 5/00* (2013.01); *B05D 7/546* (2013.01); *C08F 2/48* (2013.01); *C08J 7/18* (2013.01); *A61M 2207/00* (2013.01); *C08J 2323/28* (2013.01); *C08J 2433/16* (2013.01); *C08J 2433/26* (2013.01)

(58) Field of Classification Search
CPC ..... C08F 279/02; C08F 2/48; A61M 2207/00; A61M 5/31513; B05D 5/00; B05D 7/546; B05D 3/067; C08J 2323/28; C08J 2433/26; C08J 7/18; C08J 2433/16
USPC .............................................. 522/3, 1; 520/1
See application file for complete search history.

(56) References Cited

U.S. PATENT DOCUMENTS

| | | | |
|---|---|---|---|
| 3,418,066 A | | 12/1968 | Caldwell et al. |
| 5,100,689 A | | 3/1992 | Goldberg et al. |
| 5,340,879 A | | 8/1994 | Audenaert et al. |
| 5,453,467 A | * | 9/1995 | Bamford ............. A61L 33/0088 |
| | | | 427/2.24 |
| 5,637,460 A | | 6/1997 | Swan et al. |
| 5,688,252 A | | 11/1997 | Matsuda et al. |
| 5,885,566 A | | 3/1999 | Goldberg |
| 5,889,073 A | | 3/1999 | Zhang et al. |
| 5,967,714 A | | 10/1999 | Ottersbach et al. |
| 6,001,894 A | * | 12/1999 | Ottersbach ................. C08J 7/18 |
| | | | 427/520 |
| 6,188,075 B1 | | 2/2001 | Takayama et al. |
| 6,203,856 B1 | | 3/2001 | Ottersbach et al. |
| 6,228,172 B1 | | 5/2001 | Taylor et al. |
| 6,358,557 B1 | | 3/2002 | Wang et al. |
| 6,808,738 B2 | | 10/2004 | Ditizio et al. |
| 7,348,055 B2 | | 3/2008 | Chappa et al. |
| 8,299,139 B1 | | 10/2012 | Taranekar et al. |
| 8,840,927 B2 | | 9/2014 | Ditizio et al. |
| 9,339,845 B2 | | 5/2016 | Minagawa |

(Continued)

FOREIGN PATENT DOCUMENTS

| | | |
|---|---|---|
| CN | 101565489 A | 10/2009 |
| CN | 102382291 A | 3/2012 |

(Continued)

OTHER PUBLICATIONS

Minegawa, WO 2012/165525 Machine Translation, Dec. 6, 2012.*
Minagawa, WO 2012165525 Machine Translation, Dec. 6, 2012.*
International Search Report, issued Feb. 25, 2014, for International Application No. PCT/JP2013/082409.
Allmér et al., "Surface Modification of Polymers. I. Vapour Phase Photografting with Acrylic Acid," Journal of Polymer Science: Part A: Polymer Chemistry, vol. 26, 1988, pp. 2099-2111.
International Search Report issued in PCT/JP2013/074219 dated Dec. 3, 2013.

(Continued)

*Primary Examiner* — Jessica E Whiteley
(74) *Attorney, Agent, or Firm* — Birch, Stewart, Kolasch & Birch, LLP

(57) ABSTRACT

The present invention provides methods of modifying the surfaces of a plurality of three-dimensional objects at the same time to provide good sliding properties, good durability after repeated sliding, good sealing properties, and the like, and also provides gaskets for syringes obtained by such methods. The present invention relates to a method for modifying the surfaces of a plurality of three-dimensional objects including: a step 1 of immersing a plurality of three-dimensional objects in a photopolymerizable monomer-containing liquid; and a step 2 of polymerizing the photopolymerizable monomer by photoirradiation while rotating a vessel containing the plurality of three-dimensional objects and the photopolymerizable monomer-containing liquid, to grow polymer chains on the surfaces of the plurality of three-dimensional objects.

21 Claims, 3 Drawing Sheets

(56) References Cited

U.S. PATENT DOCUMENTS

| | | |
|---|---|---|
| 9,469,736 B2 | 10/2016 | Minagawa |
| 2002/0161065 A1 | 10/2002 | Ditizio et al. |
| 2004/0086568 A1* | 5/2004 | Ditizio .................. A61L 27/34 424/486 |
| 2004/0106732 A1 | 6/2004 | Tsuji et al. |
| 2005/0137355 A1 | 6/2005 | Buckanin et al. |
| 2006/0155057 A1 | 7/2006 | Hermeling et al. |
| 2007/0003592 A1 | 1/2007 | Hissink |
| 2007/0116971 A1 | 5/2007 | Yoshikawa et al. |
| 2008/0016644 A1 | 1/2008 | Mizote et al. |
| 2008/0103287 A1 | 5/2008 | Chino et al. |
| 2008/0312377 A1 | 12/2008 | Schmidt et al. |
| 2009/0169715 A1 | 7/2009 | Dias et al. |
| 2009/0239089 A1 | 9/2009 | Agata et al. |
| 2010/0255336 A1 | 10/2010 | Zabinski |
| 2011/0160357 A1 | 6/2011 | Gerster et al. |
| 2011/0274940 A1 | 11/2011 | Kyomoto et al. |
| 2012/0021151 A1 | 1/2012 | Tatarka et al. |
| 2012/0100369 A1 | 4/2012 | Hanazawa et al. |
| 2013/0203883 A1 | 8/2013 | Minagawa |
| 2013/0274367 A1 | 10/2013 | Minagawa et al. |
| 2013/0310772 A1 | 11/2013 | Minagawa |
| 2014/0039084 A1 | 2/2014 | Minagawa |
| 2014/0128493 A1 | 5/2014 | Minagawa |
| 2015/0203612 A1 | 7/2015 | Minagawa |

FOREIGN PATENT DOCUMENTS

| | | |
|---|---|---|
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 61-209667 A | 9/1986 |
| JP | 62-87163 A | 4/1987 |
| JP | 63-92658 A | 4/1988 |
| JP | 5-43634 A | 2/1993 |
| JP | 5-179055 A | 7/1993 |
| JP | 6-25450 A | 2/1994 |
| JP | 06-510322 A | 11/1994 |
| JP | 7-100744 B2 | 11/1995 |
| JP | 8-1793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-90500 A | 4/1998 |
| JP | 10-251350 A | 9/1998 |
| JP | 10-298320 A | 11/1998 |
| JP | 11-192305 A | 7/1999 |
| JP | 2000-273229 A | 10/2000 |
| JP | 2001-31871 A | 2/2001 |
| JP | 2001-46956 A | 2/2001 |
| JP | 2001-95621 A | 4/2001 |
| JP | 2002-145971 A | 5/2002 |
| JP | 2002-544346 A | 12/2002 |
| JP | 2003-2903 A | 1/2003 |
| JP | 2003/510378 A | 3/2003 |
| JP | 2004-528418 A | 9/2004 |
| JP | 2004-298220 A | 10/2004 |
| JP | 2005-516736 A | 6/2005 |
| JP | 2005-213516 A | 8/2005 |
| JP | 2005-523981 A | 8/2005 |
| JP | 2005-253538 A | 9/2005 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2012-105579 A | 6/2012 |
| JP | 2012-162646 A | 8/2012 |
| JP | 2013-159629 A | 8/2013 |
| JP | 2013-208777 A | 10/2013 |
| JP | 2013-237801 A | 11/2013 |
| JP | 2013-237802 A | 11/2013 |
| WO | WO 93/05081 A1 | 3/1993 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2010/058848 A1 | 5/2010 |
| WO | WO 2010/131652 A1 | 11/2010 |
| WO | WO 2011/038483 A1 | 4/2011 |
| WO | WO 2012/091169 A1 | 7/2012 |
| WO | 2012-165525 * | 12/2012 |
| WO | 2012165525 * | 12/2012 |
| WO | WO 2012/165525 A1 | 12/2012 |

OTHER PUBLICATIONS

International Search Report, mailed on Jul. 24, 2012, for International Application No. PCT/JP2012/064030.
U.S. Non-Final Office Action, issued May 8, 2015, for U.S. Appl. No. 13/756,837.
U.S. Non-Final Office Action, issued Oct. 20, 2014, for U.S. Appl. No. 13/756,837.
U.S. Notice of Allowance, issued Dec. 26, 2014, for U.S. Appl. No. 13/956,974.
U.S. Office Action (Requirement for Restriction/Election), issued May 9, 2014, for U.S. Appl. No. 13/956,974.
U.S. Office Action dated Jun. 24, 2015, for U.S. Appl. No. 14/118,136.
U.S. Office Action dated Sep. 21, 2015, for U.S. Appl. No. 14/107,746.
U.S. Office Action, issued Apr. 17, 2015, for U.S. Appl. No. 13/775,451.
U.S. Office Action, issued Aug. 25, 2014, for U.S. Appl. No. 13/956,974.
International Search Report and Written Opinion of the International Searching Authority, issued in PCT/JP2014/079947, dated Jan. 20, 2015.
International Search Report, issued in PCT/JP2014/063268, dated Aug. 19, 2014.
U.S. Office Action, issued Nov. 3, 2016, for U.S. Appl. No. 14/896,096.
International Search Report and English translation thereof, dated Jan. 21, 2014, for International Application No. PCT/JP2013/081090.
Jinan Haohua Industry Co., Ltd., "Ethanaminum, N,N,N-trimethyl-2-[(2-methyl-1-oxo-2-propen-1-yl) oxy]-, chloride (1:1)," CAS: 5039-78-1, Product Information Inquiry Description, found online on Dec. 27, 2016, pp. 1-2 (3 pages), http://guide7932.guidechem.com/pro-show2436647.html.

* cited by examiner (a)

(b)

(a)

(b)

SURFACE MODIFICATION METHOD FOR THREE-DIMENSIONAL OBJECT AND SYRINGE GASKET

TECHNICAL FIELD

The present invention relates to methods for modifying the surfaces of a plurality of three-dimensional objects, and gaskets for syringes having a surface modified by such a method.

BACKGROUND ART

Various products formed of three-dimensional objects, such as gaskets which are integrated with a syringe plunger to form a seal between the plunger and the syringe barrel, have been proposed. Various surface-modified products have been offered as such three-dimensional objects, and they are used for a variety of applications. In commonly used conventional methods for surface modification, three-dimensional objects are individually modified.

Such methods have problems in that they have poor productivity, are unsuitable for mass production and difficult to put to practical use and that the processes for individual surface modification cost a lot and have poor economic efficiency, etc.

SUMMARY OF INVENTION

Technical Problem

The present invention aims to solve the above problems and provide methods of modifying the surfaces of a plurality of three-dimensional objects at the same time to provide good sliding properties, good durability after repeated sliding, good sealing properties, and the like, and also provide gaskets for syringes obtained by such methods.

Solution to Problem

The present invention relates to a method for modifying surfaces of a plurality of three-dimensional objects, including: a step 1 of immersing a plurality of three-dimensional objects in a photopolymerizable monomer-containing liquid; and a step 2 of polymerizing the photopolymerizable monomer by photoirradiation while rotating a vessel containing the plurality of three-dimensional objects and the photopolymerizable monomer-containing liquid, to grow polymer chains on surfaces of the plurality of three-dimensional objects.

The photopolymerizable monomer is preferably at least one selected from the group consisting of acrylic acid, acrylic acid esters, acrylic acid alkali metal salts, acrylic acid amine salts, methacrylic acid, methacrylic acid esters, methacrylic acid alkali metal salts, methacrylic acid amine salts, acrylonitrile, acrylamide, dimethylacrylamide, diethylacrylamide, isopropylacrylamide, hydroxyacrylamide, hydroxyethylacrylamide, acryloylmorpholine, methacrylonitrile, methacrylamide, dimethylmethacrylamide, diethylmethacrylamide, isopropylmethacrylamide, hydroxymethacrylamide, hydroxyethylmethacrylamide, methacryloylmorpholine, and zwitterionic monomers having a carboxybetaine group, a sulfoxybetaine group, or a phosphobetaine group in a side chain.

The photopolymerizable monomer-containing liquid preferably contains a polymerization initiator. The polymerization initiator is preferably at least one of a benzophenone compound or a thioxanthone compound.

The photopolymerizable monomer-containing liquid preferably contains 20 to 500 ppm of a polymerization inhibitor.

The vessel is preferably rotated at a rotation speed of 20 to 1000 rpm.

The vessel is preferably rotated while rotation speed of the vessel is intermittently changed.

The vessel is preferably rotated while rotation direction of the vessel is intermittently changed.

The vessel preferably has a protrusion on an inner surface.

Light used in the photoirradiation preferably has a wavelength of 300 to 400 nm.

In the surface modification method, preferably, an inert gas is inserted into the reaction vessel and the reaction mixture during or before the photoirradiation, and the monomer is polymerized in an atmosphere replaced with the inert gas.

Prior to the step 1, a polymerization initiator is preferably preliminarily adsorbed to the surfaces of the three-dimensional objects. Preferably, prior to the step 1, a polymerization initiator is preliminarily adsorbed to the surfaces of the three-dimensional objects, and fixed to the surfaces by photoirradiation.

The surface modification method preferably includes: a step 3 of immersing the plurality of three-dimensional objects having polymer chains obtained in the step 2 in a functional photopolymerizable monomer-containing liquid, or applying a functional photopolymerizable monomer-containing liquid to the plurality of three-dimensional objects having polymer chains obtained in the step 2; and a step 4 of polymerizing the functional photopolymerizable monomer by photoirradiation while rotating a vessel containing the plurality of three-dimensional objects having polymer chains and the functional photopolymerizable monomer-containing liquid, to grow functional polymer chains.

The functional photopolymerizable monomer is preferably an acrylate or methacrylate containing a fluoroalkyl group, a fluoroalkylether group, or a dimethylsiloxane group.

The present invention also relates to a gasket for syringes, having a surface at least partly modified by the surface modification method.

Advantageous Effects of Invention

The present invention provides methods for modifying the surfaces of a plurality of three-dimensional objects, including: a step 1 of immersing a plurality of three-dimensional objects in a photopolymerizable monomer-containing liquid; and a step 2 of polymerizing the photopolymerizable monomer by photoirradiation while rotating a vessel containing the plurality of three-dimensional objects and the photopolymerizable monomer-containing liquid, to grow polymer chains on the surfaces of the plurality of three-dimensional objects. In such methods, photopolymerizing polymer chains are formed on the surfaces of the plurality of three-dimensional objects at the same time with reduced variations and, therefore, excellent sliding properties, excellent durability after repeated sliding, and excellent sealing properties can be imparted to each of the three-dimensional objects. Accordingly, such surface modification methods can be used to produce with high productivity a plurality of surface-modified elastic bodies such as gaskets for syringes which are excellent in these properties.

DESCRIPTION OF EMBODIMENTS

Figure 1:
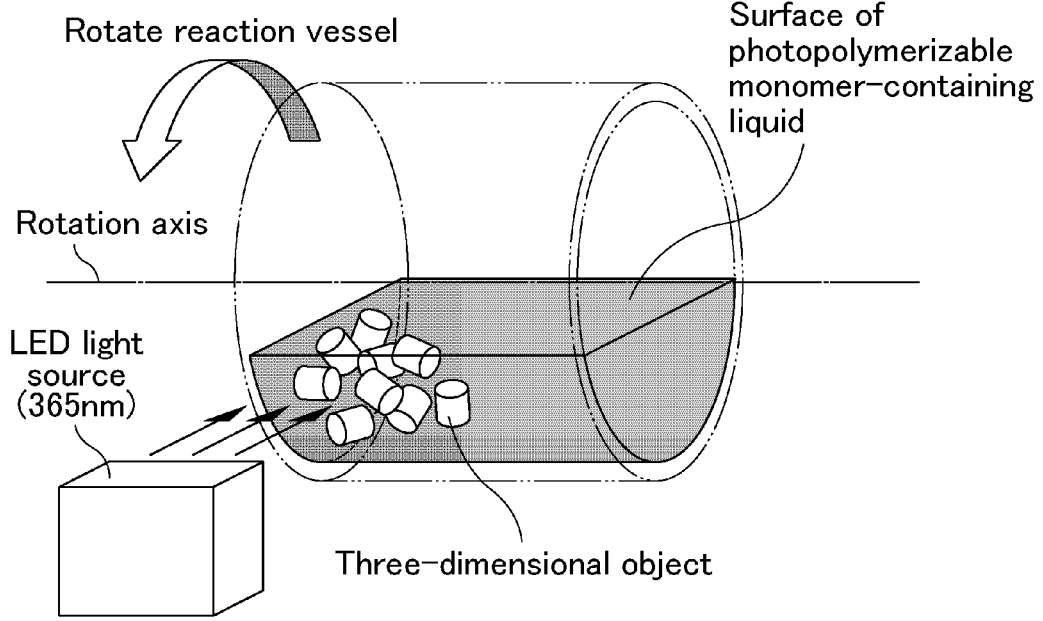
FIG. 1 is an exemplary view schematically illustrating radical polymerization in the step 2 (rotation axis: horizontal).
Figure 1:
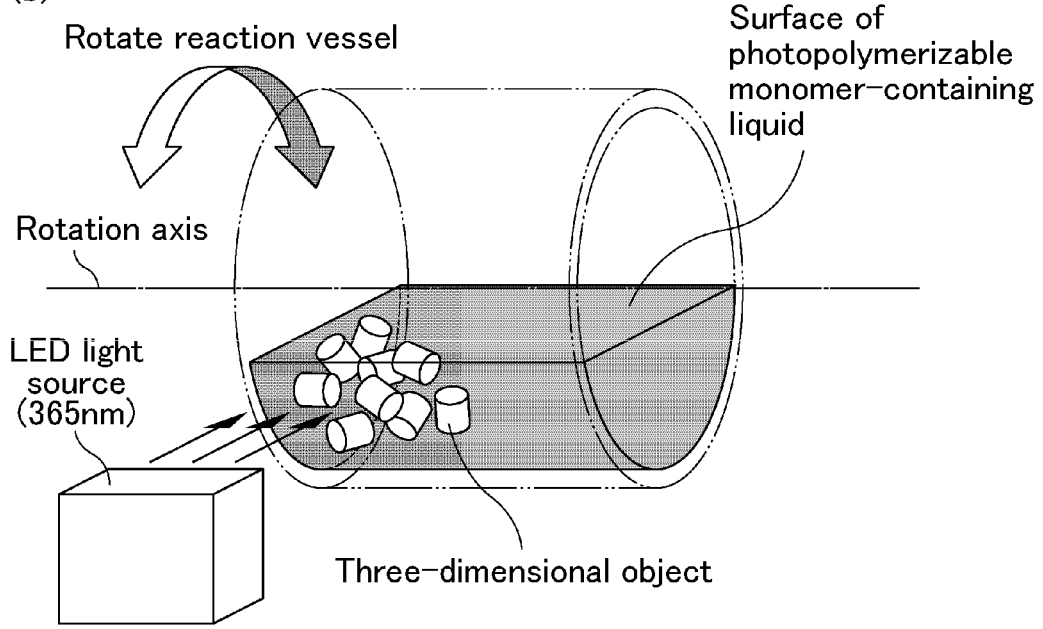

The methods for modifying the surfaces of three-dimensional objects of the present invention include: a step 1 of immersing a plurality of three-dimensional objects in a photopolymerizable monomer-containing liquid; and a step 2 of polymerizing the photopolymerizable monomer by photoirradiation while rotating a vessel containing the plurality of three-dimensional objects and the photopolymerizable monomer-containing liquid, to grow polymer chains on the surfaces of the plurality of three-dimensional objects.

As described above, since methods of individually modifying three-dimensional objects have problems such as poor productivity and poor economic efficiency, a method of modifying a plurality of three-dimensional objects at the same time has been desired. In the conventional vortex stirring method, specifically, in the method of stirring a plurality of three-dimensional objects and a photopolymerizable monomer-containing liquid in a vessel with a stirrer or the like, if a large number of three-dimensional objects are used, they may not be sufficiently stirred in a vortex, and it is thus difficult to uniformly surface-modify them. In the methods of the present invention, while a vessel containing a plurality of three-dimensional objects and a photopolymerizable monomer-containing liquid is rotated, the photopolymerizable monomer is polymerized by photoirradiation. Such methods allow even a large number of three-dimensional objects to be uniformly surface-modified. Additionally, even when only a small amount of photopolymerizable monomer-containing liquid is used, polymer chains can be formed uniformly on individual three-dimensional objects. Accordingly, efficient surface modification is enabled.

In the step 1, a plurality of three-dimensional objects are immersed in a photopolymerizable monomer-containing liquid.

The three-dimensional object may be, for example, a rubber vulcanizate or a thermoplastic elastomer, and those containing a carbon atom adjacent to a double bond (i.e., allylic carbon atom) can be suitably used.

Examples of the rubber of the rubber vulcanizate include diene rubbers such as styrene-butadiene rubber, polybutadiene rubber, polyisoprene rubber, natural rubber, and deproteinized natural rubber; and butyl rubber and halogenated butyl rubber which have a degree of unsaturation of a few percent of isoprene units. The butyl rubber or halogenated butyl rubber, if used, is preferably cross-linked by triazine because the amount of matter extracted from the rubber vulcanizate is small. In this case, the rubber may contain an acid acceptor. Examples of suitable acid acceptors include hydrotalcite and magnesium carbonate.

When other rubbers are used, they are preferably vulcanized with sulfur. In such cases, compounding ingredients commonly used for sulfur vulcanization may be added, such as vulcanization accelerators, zinc oxide, filler, and silane coupling agents. Suitable examples of the filler include carbon black, silica, clay, talc, and calcium carbonate.

The vulcanization conditions for the rubber may be appropriately chosen. The rubber is preferably vulcanized at 150° C. or higher, more preferably 170° C. or higher, still more preferably 175° C. or higher.

Examples of the thermoplastic elastomer include polymer compounds that have rubber elasticity at room temperature owing to aggregates of plastic components (hard segments) serving as crosslinking points (e.g., thermoplastic elastomers (TPE) such as styrene-butadiene-styrene copolymer); and polymer compounds having rubber elasticity, obtained by mixing a thermoplastic component and a rubber component and dynamically crosslinking the mixture by a crosslinking agent (e.g., thermoplastic elastomers (TPV) such as polymer alloys containing a styrenic block copolymer or olefinic resin and a cross-linked rubber component).

Other examples of suitable thermoplastic elastomers include nylon, polyester, polyurethane, polyethylene terephthalate (PET), polypropylene, and dynamically cross-linked thermoplastic elastomers thereof. Preferred among dynamically cross-linked thermoplastic elastomers are those obtained by dynamically crosslinking halogenated butyl rubber in a thermoplastic elastomer. This thermoplastic elastomer is preferably nylon, polyurethane, polypropylene, styrene-isobutylene-styrene block copolymer (SIBS), or the like.

The step 1 in which a plurality of three-dimensional objects are immersed in a photopolymerizable monomer-containing liquid, is preferably preceded by a step of forming polymerization initiation points on the surfaces of the plurality of three-dimensional objects.

The polymerization initiation points may be formed, for example, by adsorbing a polymerization initiator to the surfaces of the plurality of three-dimensional objects. Examples of the polymerization initiator include carbonyl compounds, organic sulfur compounds such as tetraethylthiuram disulfide, persulfides, redox compounds, azo compounds, diazo compounds, halogen compounds, and photoreductive pigments. Carbonyl compounds are especially preferred.

The carbonyl compound used as the polymerization initiator is preferably benzophenone or its derivative, and may suitably be a benzophenone compound represented by the following formula:

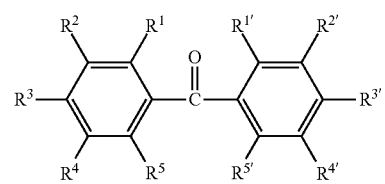

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary to tertiary amino group, a mercapto group, or a hydrocarbon group optionally containing an oxygen atom, a nitrogen atom, or a sulfur atom; and any adjacent two of them may be joined together to form a cyclic structure together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Among these, benzophenone, xanthone, and 9-fluorenone are particularly preferred because good polymer brushes can be formed. Other examples of suitable benzophenone compounds include fluorobenzophenone compounds, such as 2,3,4,5,6-pentafluorobenzophenone and decafluorobenzophenone.

Thioxanthone compounds can also be suitably used as the polymerization initiator because they provide a high polymerization rate and also can easily be adsorbed on and/or reacted with rubber or the like. For example, compounds represented by the following formula can be suitably used.

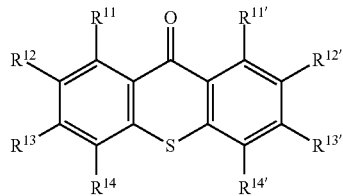

In the formula, $R^{11}$ to $R^{14}$ and $R^{11'}$ to $R^{14'}$ are the same as or different from one another and each represent a hydrogen atom, a halogen atom, an alkyl group, a cyclic alkyl group, an aryl group, an alkenyl group, an alkoxy group, or an aryloxy group.

Examples of thioxanthone compounds represented by the formula include thioxanthone, 2-isopropylthioxanthone, 4-isopropylthioxanthone, 2,3-dimethylthioxanthone, 2,4-dimethylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are the compounds in which one or two, particularly two of $R^{11}$ to $R^{14}$ and $R^{11'}$ to $R^{14'}$ are substituted with alkyl groups, and more preferred is 2,4-diethylthioxanthone.

The polymerization initiator, e.g., benzophenone compound or thioxanthone compounds, may be adsorbed to the surfaces of the three-dimensional objects by conventionally known methods. In the case of using a benzophenone compound or a thioxanthone compound, for example, the benzophenone compound or thioxanthone compound is dissolved in an organic solvent to prepare a solution; a surface portion of the three-dimensional object to be modified is treated with this solution so that the compound is adsorbed on the surface; and, if necessary, the organic solvent is evaporated off by drying, whereby polymerization initiation points are formed. The surface-treating method is not particularly limited as long as the solution of the benzophenone compound or thioxanthone compound can be brought into contact with the surface of the three-dimensional object. Suitable examples of the method include application or spraying of the benzophenone or thioxanthone compound solution, and immersion into the solution. If only part of the surface needs to be modified, it is sufficient to adsorb the polymerization initiator only on the necessary part of the surface. In this case, for example, application of the solution or spraying of the solution is suitable. Examples of the solvent include methanol, ethanol, acetone, benzene, toluene, methyl ethyl ketone, ethyl acetate, and THF. Acetone is preferred because it does not swell the three-dimensional object and it can be rapidly dried and evaporated off.

Moreover, after the target portion to be modified is surface-treated with the benzophenone or thioxanthone compound solution so that the polymerization initiator is adsorbed, the polymerization initiator is preferably further chemically bonded to the surface of the three-dimensional object by photoirradiation. For example, the benzophenone or thioxanthone compound solution can be fixed to the surface by irradiation with ultraviolet light having a wavelength of 300 to 450 nm, preferably 300 to 400 nm, more preferably 350 to 400 nm. During the formation and the fixing of the polymerization initiator, hydrogen is abstracted from the rubber surface, and a carbon atom on the rubber surface is then covalently bonded to the carbon atom in C=O of benzophenone while the abstracted hydrogen is bonded to the oxygen atom in C=O to form C—O—H. Moreover, since the hydrogen abstraction reaction selectively occurs on allylic hydrogen atoms in the object to be modified, the rubber preferably contains a butadiene or isoprene unit that contains an allylic hydrogen atom.

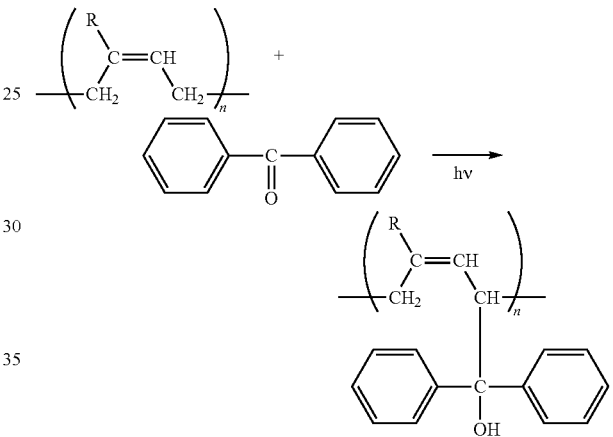

R: Hydrogen or C1-C4 alkyl group

In particular, the polymerization initiation points are preferably formed by treating the surfaces of the plurality of three-dimensional objects with the polymerization initiator so that the polymerization initiator is adsorbed on the surfaces, and then irradiating the treated surfaces with LED light having a wavelength of 300 to 400 nm. Particularly preferably, the surfaces of the three-dimensional objects are treated with, for example, the benzophenone or thioxanthone compound solution to adsorb the polymerization initiator, and then the treated surfaces are further irradiated with LED light having a wavelength of 300 to 400 nm so that the adsorbed polymerization initiator is chemically bonded to the surfaces. The LED light suitably has a wavelength of 355 to 380 nm.

Examples of the photopolymerizable monomer used in the step 1 include (meth)acrylic acid, (meth)acrylic acid esters (e.g. methoxyethyl (meth)acrylate, hydroxyethyl (meth)acrylate), (meth)acrylic acid alkali metal salts, (meth)acrylic acid amine salts, and (meth)acrylonitrile. Other examples include monomers containing a C—N bond in the molecule. Examples of the monomers containing a C—N bond in the molecule include (meth)acrylamide; N-alkyl substituted (meth)acrylamide derivatives (e.g. N-ethyl (meth)acrylamide, N-n-propyl(meth)acrylamide, N-isopropyl(meth)acrylamide, N-cyclopropyl(meth)acrylamide, N-ethoxyethyl(meth)acrylamide); N,N-dialkyl substituted (meth)acrylamide derivatives (e.g. N,N-dimethyl(meth)

acrylamide, N,N-ethylmethyl(meth)acrylamide, N,N-diethyl(meth)acrylamide); hydroxy(meth)acrylamide; hydroxy(meth)acrylamide derivatives (e.g. N-hydroxyethyl(meth)acrylamide); and cyclic group-containing (meth)acrylamide derivatives (e.g. (meth)acryloylmorpholine). Preferred among these are (meth)acrylic acid, (meth)acrylic acid esters, (meth)acrylic acid alkali metal salts, (meth)acrylic acid amine salts, (meth)acrylonitrile, (meth)acrylamide, dimethyl(meth)acrylamide, diethyl(meth)acrylamide, isopropyl(meth)acrylamide, hydroxy(meth)acrylamide, hydroxyethyl(meth)acrylamide, and (meth)acryloylmorpholine. More preferred is (meth)acrylamide. Particularly preferred is acrylamide.

Other preferred photopolymerizable monomers are zwitterionic monomers having a carboxybetaine, sulfoxybetaine, or phosphobetaine group in a side chain. Preferred are 2-(meth)acryloyloxyethyl phosphorylcholine, 2-(meth)acryloyloxyethyl carboxybetaine, and 2-(meth)acryloyloxyethyl sulfobetaine particularly because of their low protein adsorbability.

As described above, a polymerization initiator may be preliminarily adsorbed and fixed to the surfaces of the three-dimensional objects. Alternatively, the liquid containing a photopolymerizable monomer (photopolymerizable monomer-containing liquid) used in the step 1 may contain a polymerization initiator. In this case, the polymerization initiator is irradiated with light so that the initiator generates radicals, which are then allowed to abstract hydrogen from the surface of the three-dimensional object so that radicals are generated on the surface of the three-dimensional object, and graft polymerization of the monomer is initiated from the radicals formed on the surface. Accordingly, the polymerization initiator is suitably a hydrogen abstraction type polymerization initiator such as the aforementioned benzophenone or thioxanthone compound.

Moreover, preferably, the photopolymerizable monomer-containing liquid contains a polymerization inhibitor, and the monomer is polymerized in the presence of the polymerization inhibitor. The polymerization inhibitor is preferably 4-methylphenol. The amount of the polymerization inhibitor in the photopolymerizable monomer-containing liquid is preferably 20 to 500 ppm.

In the step 1, a plurality of three-dimensional objects are immersed in a photopolymerizable monomer-containing liquid. The immersion method is not particularly limited, and any method that allows the modification target, i.e., the plurality of three-dimensional objects to be immersed in the photopolymerizable monomer-containing liquid may be used. The immersion in the step 1 includes not only a case where all of the plurality of three-dimensional objects are immersed but also a case where the plurality of three-dimensional objects are at least partly immersed (e.g., only a part of the plurality of three-dimensional objects is immersed).

After the immersion in the step 1, the step 2 is performed in which polymer chains are grown on the surfaces of the plurality of three-dimensional objects by polymerizing the photopolymerizable monomer by photoirradiation while rotating a vessel containing the plurality of three-dimensional objects and the photopolymerizable monomer-containing liquid.

Figure 2:
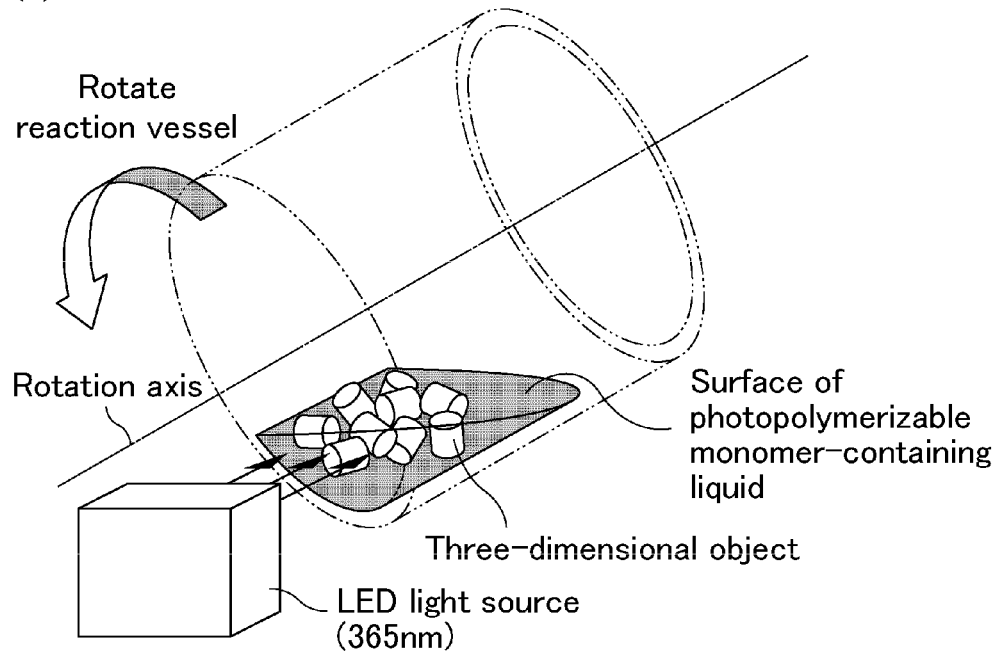
FIG. 2 is an exemplary view schematically illustrating radical polymerization in the step 2 (rotation axis: inclined).
Figure 2:
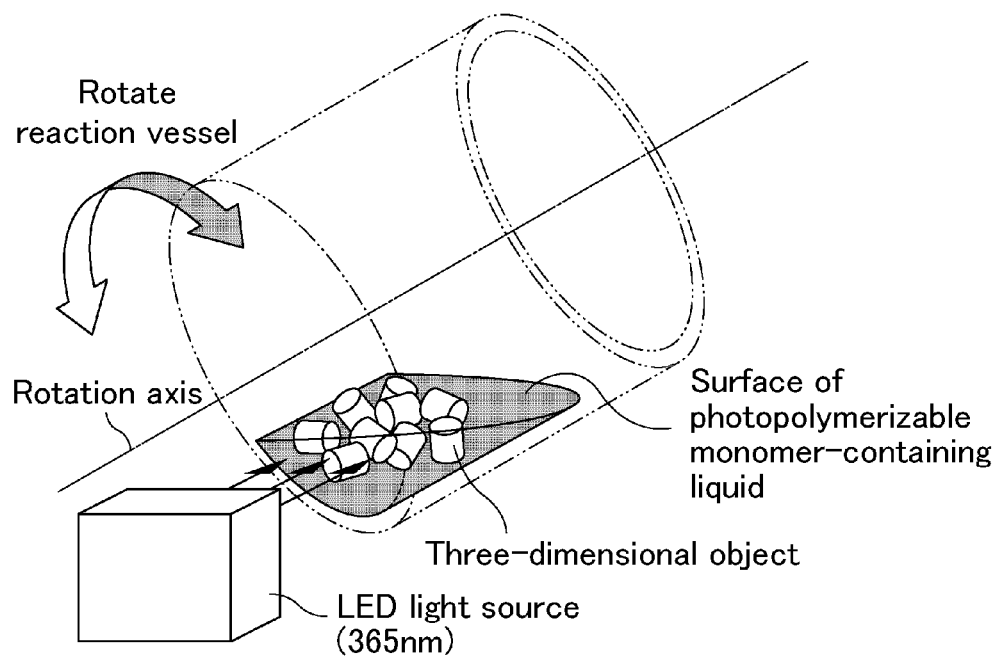

In the step 2, the method of rotating the vessel containing the plurality of three-dimensional objects and the photopolymerizable monomer-containing liquid is not particularly limited, and conventionally known methods may be used. Examples include a method of rotation around a rotation axis in a horizontal direction (parallel direction) relative to the surface of the photopolymerizable monomer-containing liquid as illustrated in FIG. 1, and a method of rotation around a rotation axis in an inclined direction (at an incline) relative to the surface of the photopolymerizable monomer-containing liquid as illustrated in FIG. 2.

When the rotation axis is inclined, the angle of inclination may be appropriately chosen. The angle of inclination is preferably 0 to 70 degrees, more preferably 0 to 50 degrees relative to the surface of the photopolymerizable monomer-containing liquid because polymer chains can be uniformly formed on the surfaces of the individual three-dimensional objects.

In the step 2, various rotation conditions may be appropriately controlled. For example, the rotation speed of the vessel is preferably 20 to 1000 rpm. This enables revolution and rotation of the individual three-dimensional objects so that their surfaces can be largely uniformly irradiated with light. The vessel may be rotated while the rotation speed of the vessel is intermittently changed. Moreover, the vessel may be rotated while the rotation direction of the vessel is intermittently changed, as illustrated in FIG. 1(b) and FIG. 2(b). In such a case, the three-dimensional objects rise along the wall surface of the vessel and then fall, and this cycle is repeated so that the positions or directions of the three-dimensional objects are varied. Accordingly, their surfaces can be largely uniformly irradiated with light.

Figure 3:
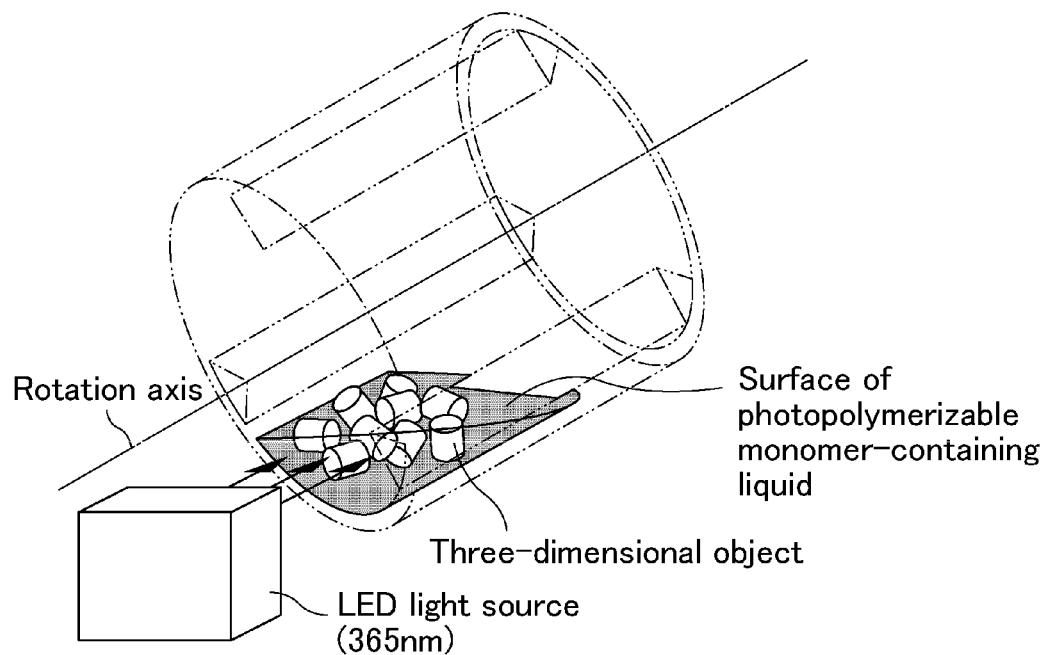
FIG. 3 is an exemplary view of a vessel having a protrusion on the inner surface.

In the step 2, in particular, the vessel used preferably has a protrusion on the inner surface as illustrated in FIG. 3. If such a vessel with a protrusion is used in the methods as illustrated in FIGS. 1 and 2, the three-dimensional objects collide with the protrusion upon the rotation, so that the positions or directions of the objects are effectively changed. Accordingly, their surfaces can be more uniformly irradiated with light.

The shape and orientation of the protrusion are not particularly limited. Preferred are those in which the positions or directions of the three-dimensional objects are effectively changed by collision with the protrusion upon the rotation. For example, the protrusion suitably has a shape that serves like a baffle in the rotation direction. Specific examples include a protrusion having a substantially triangular prism shape as illustrated in FIG. 3, as well as protrusions having a substantially rectangular parallelepiped shape and a substantially plate shape.

The number of protrusions on the inner surface is not particularly limited, and may be appropriately adjusted depending on the number or size of the three-dimensional objects. Preferably, the number of protrusions is around 2 to 10. The size of each protrusion may also be appropriately chosen in view of the size of the vessel, photoirradiation uniformity, and the like.

In the radical polymerization of the photopolymerizable monomer in the step 2, for example, while being rotated, a vessel in which a part or all of the plurality of three-dimensional objects to which a benzophenone or thioxanthone compound or the like is adsorbed or covalently bonded are immersed in the photopolymerizable monomer-containing liquid is irradiated with light such as, ultraviolet rays. This allows the radical polymerization (photoradical polymerization) to proceed to grow polymer chains on the surfaces of the individual three-dimensional objects.

In the present invention, the radical polymerization of the monomer is allowed to proceed by photoirradiation after the immersion in the photopolymerizable monomer-containing liquid (e.g., the (liquid) photopolymerizable monomer or a solution thereof). Here, UV light sources with an emission wavelength mainly in the ultraviolet region, such as high pressure mercury lamps, metal halide lamps, and LED lamps, can be suitably used. The light dose may be appropriately chosen in view of polymerization time and uniformity of the reaction progress. Moreover, in order to prevent inhibition of polymerization due to active gas such as oxygen in the reaction vessel, oxygen is preferably removed from the reaction vessel and the reaction mixture during or before the photoirradiation. To this end, appropriate operations may be performed. For example, an inert gas, such as nitrogen gas or argon gas, is inserted into the reaction vessel and the reaction mixture to discharge active gas such as oxygen from the reaction system and replace the atmosphere in the reaction system with the inert gas, or the reaction vessel is evacuated and degassed of oxygen. Furthermore, in order to prevent inhibition of the reaction due to oxygen or the like, for example, a measure may appropriately be taken in which a UV light source is placed such that an air layer (oxygen content: 15% or higher) does not exist between the reaction vessel made of glass, plastics or the like and the reaction mixture or the three-dimensional objects.

In the case of irradiation with ultraviolet light, the ultraviolet light preferably has a wavelength of 300 to 450 nm, more preferably a wavelength of 300 to 400 nm. Such ultraviolet light enables polymer chains to be well formed, without variations, on the surfaces of the plurality of three-dimensional objects. Also, such ultraviolet light does not allow radicals to be generated initially from the monomer or the surfaces of the three-dimensional objects, but allows radicals to be generated only from the polymerization initiator. Ultraviolet light having a wavelength below 300 nm, unfortunately, also polymerizes the monomer alone, not starting from the surface, to form free polymers. Examples of light sources include high pressure mercury lamps, LEDs with a center wavelength of 365 nm, and LEDs with a center wavelength of 375 nm. In particular, irradiation with LED light having a wavelength of 300 to 400 nm is preferred, and irradiation with LED light having a wavelength of 355 to 380 nm is more preferred. Particularly, LEDs or the like having a center wavelength of 365 nm, which is close to the excitation wavelength (366 nm) of benzophenone, are preferred in view of efficiency. Moreover, in the case of ultraviolet rays containing light of various wavelengths (e.g., high pressure mercury lamps), they may be irradiated, for example, while blocking light of wavelengths below 300 nm by a filter.

Polymer chains formed on the surfaces of the individual three-dimensional objects in the step 2 provide excellent sliding properties and excellent durability while maintaining good sealing properties. The polymerization degree of the formed polymer chains is preferably 20 to 200000, more preferably 350 to 50000. If the polymerization degree is less than 20, the polymer chains are so short that they may be concealed by irregularities on the surfaces of the three-dimensional objects, which tends to result in failure to provide sliding properties. If the polymerization degree exceeds 200000, the amount of monomer used is increased, which tends to result in an economic disadvantage.

The polymer chains formed in the step 2 preferably each have a length of 10 to 50000 nm, more preferably 100 to 50000 nm. Polymer chains shorter than 10 nm tend not to provide good sliding properties. Polymer chains longer than 50000 nm cannot be expected to provide further improved sliding properties, while they tend to lead to an increase in the cost of raw materials because the monomer used is expensive. In addition, in such cases, surface patterns generated by the surface modification tend to be visible to the naked eye and thereby spoil the appearance and decrease sealing properties.

In the step 2, two or more kinds of photopolymerizable monomers may be radically polymerized at the same time, starting from the polymerization initiation points. Moreover, multiple kinds of polymer chains may be grown on the surfaces of the individual three-dimensional objects. In the surface modification methods, the polymer chains may be cross-linked to one another. In this case, the polymer chains may be cross-linked to one another by ionic crosslinking, or crosslinking by a hydrophilic group containing an oxygen atom. Moreover, in the polymerization, a small amount of a compound having at least two vinyl groups in a molecule may be added to introduce crosslinks between the polymer chains during the polymerization. The compound having at least two vinyl groups in a molecule is preferably N,N'-methylenebisacrylamide or the like.

FIGS. 1 and 2 are schematic views specifically showing examples of the radical polymerization in the step 2. Specifically, in the steps shown in these figures, while a vessel in which a plurality of three-dimensional objects are immersed in a photopolymerizable monomer-containing liquid is rotated around a rotation axis in a horizontal direction or inclined direction, the surfaces of the individual three-dimensional objects are largely uniformly irradiated with ultraviolet rays (365 nm UV light). This allows the radical polymerization of the photopolymerizable monomer to proceed on the surfaces of the individual three-dimensional objects to grow polymer chains on the surfaces. In this manner, a plurality of surface-modified elastic bodies such as gaskets for syringes in which polymer chains are formed without variations on the surfaces of a plurality of three-dimensional objects can be simultaneously produced. In FIGS. 1 and 2, if a vessel or the like having a protrusion as illustrated in FIG. 3 is used, then polymer chains with sufficiently reduced variations can be formed. Thus, a plurality of uniform surface-modified elastic bodies can be more efficiently produced.

In the present invention, after a plurality of three-dimensional objects having polymer chains are prepared in the step 2, the following step 3 and step 4 may further be performed: a step 3 of immersing the objects in a functional photopolymerizable monomer-containing liquid or applying a functional photopolymerizable monomer-containing liquid to the objects; and a step 4 of polymerizing the functional photopolymerizable monomer by photoirradiation while rotating a vessel containing the plurality of three-dimensional objects having polymer chains and the functional photopolymerizable monomer-containing liquid, to grow functional polymer chains. With these steps, functional polymer chains are further formed to impart desired properties.

Prior to the step 3, preferably, a polymerization initiator is preliminarily adsorbed to the surfaces of the polymer chains of the plurality of three-dimensional objects having polymer chains prepared in the step 2, or a polymerization initiator is preliminarily adsorbed to the surfaces of the polymer chains of the plurality of three-dimensional objects having polymer chains prepared in the step 2, followed by fixing the polymerization initiator to the surfaces by photoirradiation. The method of adsorbing the polymerization initiator to the surfaces of the polymer chains and the method of fixing the polymerization initiator after adsorption may be carried out in the same manner as those prior to the step 1.

As mentioned above, a polymerization initiator may be preliminarily adsorbed and fixed to the surfaces of the three-dimensional objects. Alternatively, the liquid containing a functional photopolymerizable monomer (functional photopolymerizable monomer-containing liquid) used in the step 3 may contain a polymerization initiator.

The functional photopolymerizable monomer is not particularly limited, and may be appropriately selected depending on the desired properties. Examples include acrylates or methacrylates containing a fluoroalkyl group, a fluoroalkylether group, or a dimethylsiloxane group.

The surface modification methods can be applied to a plurality of three-dimensional objects to produce a plurality of surface-modified elastic bodies at the same time. For example, surface-modified elastic bodies that are excellent in sliding properties in the presence of water or in a dry state can be obtained. These surface-modified elastic bodies are also excellent in that they have low friction and low water resistance or drag. Moreover, the methods may be applied to at least a part of a three-dimensional solid (e.g. elastic body) to obtain a surface-modified elastic body with modified properties. Furthermore, preferred examples of such surface-modified elastic bodies include polymer brushes. The polymer brush as used herein means an assembly of graft polymer molecules obtained in the "grafting from" approach by surface-initiated polymerization. Moreover, the graft chains are preferably oriented in a direction substantially vertical to the surface of the three-dimensional object because, in such a case, the entropy is reduced and thus the molecular mobility of the graft chains is reduced so that sliding properties are ensured. Furthermore, semidilute or concentrated brushes having a brush density of 0.01 chains/$nm^2$ or higher are preferred.

The surface modification methods may also be applied to a plurality of three-dimensional objects to simultaneously produce a plurality of gaskets for syringes having a surface at least partly modified. At least the sliding surface portion of the gasket is preferably modified although the entire surface of the gasket may be modified.

EXAMPLES

The following will describe the present invention in more detail with reference to non-limiting examples.

Example 1

One hundred pieces of gaskets (gaskets obtained by cross-linking chlorobutyl rubber (degree of unsaturation: 1 to 2%) containing isoprene units by triazine; vulcanized at 180° C. for 10 minutes) were immersed in a 1 wt % solution of benzophenone in acetone for five minutes, taken out and dried. A 300-ml separable flask was charged with 100 ml of a 1 M acrylamide aqueous solution and 100 pcs of the gaskets dried as above. The flask was covered with a lid, and the interior of the flask was then purged with argon for 120 minutes to remove oxygen. While being rotated around a rotation axis in an inclined direction (angle of inclination: 45 degrees) in a cycle wherein the rotation speed alternated between 500 rpm and 100 rpm at one-minute intervals, the separable flask was irradiated with LED-UV light (with a wavelength of 365 nm) at an irradiation intensity of 15 mW/$cm^2$ for 150 minutes to graft polymerize the acrylamide on the gasket surfaces, whereby polymer chains were grown. The resulting gaskets were taken out, washed with water and dried. In this manner, gaskets for syringes were prepared.

Example 2

A 300-ml separable flask was charged sequentially with 100 ml of a 1 M acrylamide aqueous solution and 3 mg of benzophenone, and further charged with 100 pcs of gaskets. The flask was covered with a lid, and the interior of the flask was then purged with argon for 120 minutes to remove oxygen. While being rotated around a rotation axis in an inclined direction (angle of inclination: 45 degrees) in a cycle wherein the rotation speed alternated between 500 rpm and 100 rpm at one-minute intervals, the separable flask was irradiated with LED-UV light at an irradiation intensity of 15 mW/$cm^2$ for 150 minutes to graft polymerize the acrylamide on the gasket surfaces, whereby polymer chains were grown. The resulting gaskets were taken out, washed with water and dried. In this manner, gaskets for syringes were prepared.

Example 3

Gaskets for syringes were prepared in the same manner as in Example 2, except that rotation was carried out at a rotation speed of 500 rpm in a cycle wherein the rotation direction was inverted when the flask was rotated 70 degrees, instead of the rotation cycle wherein the rotation speed alternated between 500 rpm and 100 rpm at one-minute intervals.

Example 4

Gaskets for syringes were prepared in the same manner as in Example 1, except that the flask was evacuated by a pump for 120 minutes, instead of purging the interior of the flask with argon for 120 minutes.

Example 5

Gaskets for syringes were prepared in the same manner as in Example 1, except that the rotation speed was kept constant at 500 rpm, instead of the rotation cycle wherein the rotation speed alternated between 500 rpm and 100 rpm at one-minute intervals.

Example 6

Fifty pieces of the gaskets having a surface on which acrylamide was graft polymerized, prepared in Example 1 were immersed in a 1 wt % solution of benzophenone in acetone for five minutes, taken out and dried. Then, KY-1203 (produced by Shin-Etsu Chemical Co., Ltd., acrylate monomer containing a fluoroalkylether group) was applied to the surfaces and then dried, and the resulting gaskets were placed in a 300-ml separable flask. The flask was covered with a lid, and the interior of the flask was then purged with argon for 120 minutes to remove oxygen. While being rotated around a rotation axis in an inclined direction (angle of inclination: 45 degrees) in a cycle wherein the rotation speed alternated between 500 rpm and 100 rpm at one-minute intervals, the separable flask was irradiated with LED-UV light (with a wavelength of 365 nm) at an irradiation intensity of 15 mW/$cm^2$ for 15 minutes to graft polymerize the acrylate containing a fluoroalkylether group on the gasket surfaces, whereby polymer chains were grown. The resulting gaskets were taken out, washed with acetone and water, and dried. In this manner, gaskets for syringes were prepared.

Example 7

One hundred pieces of gaskets (gaskets obtained by cross-linking chlorobutyl rubber (degree of unsaturation: 1 to 2%) containing isoprene units by triazine; vulcanized at 180° C. for 10 minutes) were immersed in a 1 wt % solution of benzophenone in acetone for five minutes, taken out and dried. A 500-ml eggplant-shaped flask (rotary flask) with a protrusion was charged with 100 ml of a 1 M acrylamide aqueous solution and 100 pcs of the gaskets dried as above. The flask was covered with a lid, and the interior of the flask was then purged with argon for 120 minutes to remove oxygen. While being rotated at a rotation speed of 50 rpm around a rotation axis in a horizontal direction (angle of inclination: 0 degrees), the eggplant-shaped flask with a protrusion was irradiated with LED-UV light (with a wavelength of 365 nm) at an irradiation intensity of 15 mW/cm$^2$ for 150 minutes to graft polymerize the acrylamide on the gasket surfaces, whereby polymer chains were grown. The resulting gaskets were taken out, washed with water and dried. In this manner, gaskets for syringes were prepared.

Example 8

A 500-ml eggplant-shaped flask (rotary flask) with a protrusion was charged sequentially with 100 ml of a 1 M acrylamide aqueous solution and 3 mg of benzophenone, and further charged with 100 pcs of gaskets. The flask was covered with a lid, and the interior of the flask was then purged with argon for 120 minutes to remove oxygen. While being rotated at a rotation speed of 50 rpm around a rotation axis in a horizontal direction (angle of inclination: 0 degrees), the eggplant-shaped flask with a protrusion was irradiated with LED-UV light at an irradiation intensity of 15 mW/cm$^2$ for 150 minutes to graft polymerize the acrylamide on the gasket surfaces, whereby polymer chains were grown. The resulting gaskets were taken out, washed with water and dried. In this manner, gaskets for syringes were prepared.

Example 9

Gaskets for syringes were prepared in the same manner as in Example 8, except that rotation was carried out in a cycle wherein the rotation direction was inverted when the flask was rotated 70 degrees.

Example 10

Gaskets for syringes were prepared in the same manner as in Example 7, except that the flask was evacuated by a pump for 120 minutes, instead of purging the interior of the flask with argon for 120 minutes.

Example 11

Gaskets for syringes were prepared in the same manner as in Example 7, except that rotation was carried out at a rotation speed of 150 rpm.

Example 12

Gaskets for syringes were prepared in the same manner as in Example 7, except that rotation was carried out around a rotation axis in an inclined direction (angle of inclination: 15 degrees).

Example 13

Fifty pieces of the gaskets having a surface on which acrylamide was graft polymerized, prepared in Example 7 were immersed in a 1 wt % solution of benzophenone in acetone for five minutes, taken out and dried. Then, KY-1203 (produced by Shin-Etsu Chemical Co., Ltd., acrylate monomer containing a fluoroalkylether group) was applied to the surfaces and then dried, and the resulting gaskets were placed in a 500-ml eggplant-shaped flask (rotary flask) with a protrusion. The flask was covered with a lid, and the interior of the flask was then purged with argon for 120 minutes to remove oxygen. While being rotated at a rotation speed of 50 rpm around a rotation axis in an inclined direction (angle of inclination: 15 degrees), the eggplant-shaped flask (rotary flask) with a protrusion was irradiated with LED-UV light (with a wavelength of 365 nm) at an irradiation intensity of 15 mW/cm$^2$ for 15 minutes to graft polymerize the acrylate containing a fluoroalkylether group on the gasket surfaces, whereby polymer chains were grown. The resulting gaskets were taken out, washed with acetone and water, and dried. In this manner, gaskets for syringes were prepared.

Comparative Example 1

Ten pieces of gaskets (gaskets obtained by cross-linking chlorobutyl rubber (degree of unsaturation: 1 to 2%) containing isoprene units by triazine; vulcanized at 180° C. for 10 minutes) were used.

Comparative Example 2

One gasket was immersed in a 1 wt % solution of benzophenone in acetone for five minutes, taken out and dried. A 20-ml glass vessel was charged sequentially with 10 ml of a 1 M acrylamide aqueous solution and the gasket dried as above. The vessel was covered with a lid, and the interior of the vessel was then purged with argon for 60 minutes to remove oxygen. While being stirred at a rotation speed of 10 rpm, the contents of the 20-ml glass vessel were irradiated with LED-UV light at an irradiation intensity of 2 mW/cm$^2$ for 75 minutes to graft polymerize the acrylamide on the gasket surface, whereby polymer chains were grown. The resulting gasket was taken out, washed with water and dried. The above operation was repeated 10 times to prepare 10 pcs of gaskets for syringes having a grafted surface. The total polymerization time was 750 minutes (75 min×10 pcs).

The gaskets for syringes prepared in the examples and comparative examples were evaluated by the methods mentioned below.
(Length of Polymer Chain)

To determine the length of the polymer chain formed on the surface of the rubber vulcanizate, a cross section of the modified rubber having polymer chains formed thereon was measured with an SEM at an accelerating voltage of 15 kV and a magnification of 1000 times. The thickness of the polymer layer photographed was determined and taken as the length of the polymer chain.
(Friction Resistance)

To determine the friction resistance of the surface of the gaskets for syringes, the gaskets prepared in the examples and comparative examples were each inserted into a COP resin barrel of a syringe and then pushed towards the end of the barrel (push rate: 100 mm/min) using a tensile tester while friction resistance was measured. The values of the examples and comparative examples are expressed as a friction resistance index using the equation below, with the friction resistance of Comparative Example 1 set equal to 100. A lower index indicates a lower friction resistance. The friction resistance of a plurality of gaskets was measured and the average value was calculated. In addition, variations in friction resistance among the individual gaskets were evaluated based on the standard deviation of friction resistance.

(Friction resistance index)=(Friction resistance of each example)/(Friction resistance of Comparative Example 1)×100

TABLE 1

| | Example | | | | | |
|---|---|---|---|---|---|---|
| | 1 | 2 | 3 | 4 | 5 | 6 |
| Length of polymer chain (nm) | 7500 | 6500 | 8000 | 7000 | 15000 | 9500 |
| Friction resistance index | 2.20 | 2.40 | 2.10 | 2.25 | 16.3 | 1.8 |
| Variation | 0.51 | 0.6 | 0.42 | 0.63 | 12.2 | 0.5 |

| | Example | | | | | | |
|---|---|---|---|---|---|---|---|
| | 7 | 8 | 9 | 10 | 11 | 12 | 13 |
| Length of polymer chain (nm) | 6000 | 5500 | 6500 | 5500 | 5000 | 6000 | 7500 |
| Friction resistance index | 2.1 | 2.2 | 1.9 | 2.4 | 2.3 | 2.3 | 1.7 |
| Variation | 0.5 | 0.65 | 0.45 | 0.65 | 0.55 | 0.5 | 0.4 |

| | Comparative Example | |
|---|---|---|
| | 1 | 2 |
| Length of polymer chain (nm) | — | 11500 |
| Friction resistance index | 100 | 2.3 |
| Variation | 25 | 0.75 |

As shown in Table 1, the surfaces of the large number of gaskets for syringes prepared in the examples exhibited a greatly reduced average friction resistance and good sliding properties as compared to those of Comparative Example 1. In addition, since only the surfaces were modified, the surfaces of the examples had equivalent sealing properties. The surfaces of the examples also had only small variations in friction resistance, which demonstrated that a large number of surface-modified gaskets having uniform properties were produced with high productivity.

The invention claimed is:

1. A method for modifying surfaces of a plurality of three-dimensional objects, comprising:
   a step 1 of immersing a plurality of three-dimensional objects in a photopolymerizable monomer-containing liquid; and
   a step 2 of polymerizing the photopolymerizable monomer by photoirradiation while rotating a vessel containing the plurality of three-dimensional objects and the photopolymerizable monomer-containing liquid around a rotation axis inclined at 0 to 70 degrees relative to a surface of the photopolymerizable monomer-containing liquid, to grow polymer chains on surfaces of the plurality of three-dimensional objects.

2. A method for modifying surfaces of a plurality of three-dimensional objects, comprising:
   a step 1 of immersing a plurality of three-dimensional objects in a photopolymerizable monomer-containing liquid; and
   a step 2 of polymerizing the photopolymerizable monomer by photoirradiation while rotating at a rotation speed of 20 to 1000 rpm a vessel having a protrusion on an inner surface, containing the plurality of three-dimensional objects and the photopolymerizable monomer-containing liquid, to grow polymer chains on surfaces of the plurality of three-dimensional objects.

3. The method according to claim 1, wherein the vessel has a protrusion on an inner surface.

4. The method according to claim 1, wherein the photopolymerizable monomer is at least one selected from the group consisting of acrylic acid, acrylic acid esters, acrylic acid alkali metal salts, acrylic acid amine salts, methacrylic acid, methacrylic acid esters, methacrylic acid alkali metal salts, methacrylic acid amine salts, acrylonitrile, acrylamide, dimethylacrylamide, diethylacrylamide, isopropylacrylamide, hydroxyacrylamide, hydroxyethylacrylamide, acryloylmorpholine, methacrylonitrile, methacrylamide, dimethylmethacrylamide, diethylmethacrylamide, isopropylmethacrylamide, hydroxymethacrylamide, hydroxyethylmethacrylamide, methacryloylmorpholine, and zwitterionic monomers having a carboxybetaine group, a sulfoxybetaine group, or a phosphobetaine group in a side chain.

5. The method according to claim 1, wherein the photopolymerizable monomer-containing liquid contains a polymerization initiator.

6. The method according to claim 5, wherein the polymerization initiator is at least one of a benzophenone compound or a thioxanthone compound.

7. The method according to claim 1, wherein the photopolymerizable monomer-containing liquid contains 20 to 500 ppm of a polymerization inhibitor.

8. The method according to claim 1, wherein the vessel is rotated at a rotation speed of 20 to 1000 rpm.

9. The method according to claim 1, wherein the vessel is rotated while rotation speed of the vessel is intermittently changed.

10. The method according to claim 1, wherein the vessel is rotated while rotation direction of the vessel is intermittently changed.

11. The method according to claim 1, wherein light used in the photoirradiation has a wavelength of 300 to 400 nm.

12. The method according to claim 1, wherein an inert gas is inserted into the reaction vessel and the reaction mixture during or before the photoirradiation, and the monomer is polymerized in an atmosphere replaced with the inert gas.

13. The method according to claim 1, wherein prior to the step 1, a polymerization initiator is preliminarily adsorbed to the surfaces of the three-dimensional objects.

14. The method according to claim 1, wherein prior to the step 1, a polymerization initiator is preliminarily adsorbed to the surfaces of the three-dimensional objects, and fixed to the surfaces by photoirradiation.

15. The method according to claim 1, comprising:
a step 3 of immersing the plurality of three-dimensional objects having polymer chains obtained in the step 2 in a functional photopolymerizable monomer-containing liquid, or applying a functional photopolymerizable monomer-containing liquid to the plurality of three-dimensional objects having polymer chains obtained in the step 2; and
a step 4 of polymerizing the functional photopolymerizable monomer by photoirradiation while rotating a vessel containing the plurality of three-dimensional objects having polymer chains and the functional photopolymerizable monomer-containing liquid, to grow functional polymer chains.

16. The method according to claim 15, wherein the functional photopolymerizable monomer is an acrylate or methacrylate containing a fluoroalkyl group, a fluoroalkylether group, or a dimethylsiloxane group.

17. A gasket for syringes, comprising a surface at least partly modified by the method according to claim 1.

18. The method according to claim 2, wherein the vessel is rotated around a rotation axis inclined at 0 to 70 degrees relative to a surface of the photopolymerizable monomer-containing liquid.

19. The method according to claim 2, wherein the vessel is rotated while rotation speed of the vessel is intermittently changed.

20. The method according to claim 2, wherein the vessel is rotated while rotation direction of the vessel is intermittently changed.

21. The method according to claim 2, wherein the shape of the protrusion is a substantially triangular prism shape, a substantially rectangular parallelepiped shape, or a substantially plate shape.

* * * * *